United States Patent
Morrison et al.

(10) Patent No.: US 7,695,499 B2
(45) Date of Patent: Apr. 13, 2010

(54) SYSTEM, DEVICES AND METHOD FOR AUGMENTING EXISTING FUSION CONSTRUCTS

(75) Inventors: Matthew M. Morrison, Cordova, TN (US); Kent M. Anderson, Memphis, TN (US); Jonathan Dewey, Memphis, TN (US); Aurelian Bruneau, Memphis, TN (US); Fred J. Molz, IV, Collierville, TN (US); Thomas Carls, Memphis, TN (US); Eric C. Lange, Collierville, TN (US)

(73) Assignee: Warsaw Orthopedic, Inc.

( * ) Notice: Subject to any disclaimer, the term of this patent is extended or adjusted under 35 U.S.C. 154(b) by 916 days.

(21) Appl. No.: 11/118,645

(22) Filed: Apr. 29, 2005

(65) Prior Publication Data
US 2006/0247625 A1 Nov. 2, 2006

(51) Int. Cl.
*A61B 17/88* (2006.01)
(52) U.S. Cl. .................................. 606/279
(58) Field of Classification Search ............ 606/61
See application file for complete search history.

(56) References Cited

U.S. PATENT DOCUMENTS

| | | | |
|---|---|---|---|
| 4,569,338 A | 2/1986 | Edwards | |
| 4,805,602 A * | 2/1989 | Puno et al. .................. 606/61 |
| 4,827,918 A | 5/1989 | Olerud | |
| 5,047,029 A | 9/1991 | Aebi et al. | |
| 5,053,034 A | 10/1991 | Olerud | |
| 5,176,680 A | 1/1993 | Vignaud et al. | |
| 5,190,543 A | 3/1993 | Schlapfer | |
| 5,234,431 A | 8/1993 | Keller | |
| 5,254,118 A | 10/1993 | Mirkovic | |
| 5,261,909 A | 11/1993 | Sutterlin et al. | |
| 5,282,801 A | 2/1994 | Sherman | |
| 5,437,669 A * | 8/1995 | Yuan et al. .................. 606/61 |
| 5,527,314 A | 6/1996 | Brumfield et al. | |
| 5,534,002 A | 7/1996 | Brumfield et al. | |
| 5,545,166 A | 8/1996 | Howland | |
| 5,562,662 A | 10/1996 | Brumfield et al. | |
| 5,569,247 A | 10/1996 | Morrison | |
| 5,591,166 A | 1/1997 | Bernhardt et al. | |
| 5,624,441 A | 4/1997 | Sherman et al. | |
| 5,628,740 A | 5/1997 | Mullane | |
| 5,643,263 A | 7/1997 | Simonson | |
| 5,725,528 A | 3/1998 | Errico et al. | |
| 5,735,851 A | 4/1998 | Errico et al. | |
| 5,782,833 A | 7/1998 | Haider | |
| 5,800,435 A | 9/1998 | Errico et al. | |

(Continued)

OTHER PUBLICATIONS

TiMX Comprehensive Low Back System, DePuy AcroMed, © 1999.

(Continued)

*Primary Examiner*—Thomas C Barrett
*Assistant Examiner*—Nicholas Woodall

(57) ABSTRACT

One technique of the present application includes: evaluating a patient having a previously implanted spinal construct and corresponding spinal fusion from an earlier procedure and determining a spinal segment adjacent to the spinal fusion is degenerating after completion of the earlier procedure. After this determination, the previously implanted spinal construct is augmented by attaching a flexible polymer elongated member to the spinal segment adjacent to the spinal fusion with a bone fastener and by coupling the flexible polymer elongated member to one or more elements of the previously implanted spinal construct. In one form, the elongated member is at least partially comprised of polyetheretherketone.

21 Claims, 4 Drawing Sheets

U.S. PATENT DOCUMENTS

| | | |
|---|---|---|
| 5,885,285 A | 3/1999 | Simonson |
| 5,904,683 A | 5/1999 | Pohndorf et al. |
| 5,910,142 A | 6/1999 | Tatar |
| 5,938,663 A | 8/1999 | Petreto |
| 5,947,967 A | 9/1999 | Barker |
| 6,010,504 A | 1/2000 | Rogozinski |
| 6,050,997 A | 4/2000 | Mullane |
| 6,087,467 A | 7/2000 | Marrocco, III et al. |
| 6,113,601 A | 9/2000 | Tatar |
| 6,132,432 A | 10/2000 | Richelsoph |
| 6,183,473 B1 | 2/2001 | Ashman |
| 6,187,005 B1 | 2/2001 | Brace et al. |
| 6,190,388 B1 * | 2/2001 | Michelson et al. ........ 606/86 A |
| 6,210,413 B1 | 4/2001 | Justis |
| 6,248,107 B1 | 6/2001 | Foley |
| 6,267,765 B1 | 7/2001 | Taylor et al. |
| 6,315,779 B1 | 11/2001 | Morrison et al. |
| 6,352,537 B1 | 3/2002 | Strnad |
| 6,355,038 B1 | 3/2002 | Pisharodi |
| 6,478,798 B1 | 11/2002 | Howland |
| 6,485,491 B1 | 11/2002 | Farris et al. |
| 6,520,962 B1 | 2/2003 | Taylor et al. |
| 6,524,315 B1 | 2/2003 | Selvitelli et al. |
| 6,547,790 B2 | 4/2003 | Harkey, III et al. |
| 6,562,038 B1 | 5/2003 | Morrison |
| 6,582,441 B1 | 6/2003 | He et al. |
| 6,626,906 B1 | 9/2003 | Young |
| 6,685,705 B1 | 2/2004 | Taylor |
| 6,749,614 B2 | 6/2004 | Teitelbaum et al. |
| 6,770,075 B2 | 8/2004 | Howland |
| 6,783,527 B2 | 8/2004 | Drewry et al. |
| 6,875,212 B2 | 4/2005 | Shaolian et al. |
| 2002/0068975 A1 | 6/2002 | Teitelbaum et al. |
| 2002/0198526 A1 | 12/2002 | Shaolian et al. |
| 2004/0030392 A1 | 2/2004 | Lambrecht et al. |
| 2004/0034429 A1 | 2/2004 | Lambrecht et al. |
| 2004/0049189 A1 * | 3/2004 | Le Couedic et al. ........... 606/61 |
| 2004/0082954 A1 | 4/2004 | Teitelbaum et al. |
| 2004/0220668 A1 | 11/2004 | Eisermann et al. |
| 2004/0230309 A1 | 11/2004 | DiMauro et al. |
| 2005/0021031 A1 | 1/2005 | Foley et al. |
| 2005/0038432 A1 | 2/2005 | Shaolian et al. |
| 2005/0065515 A1 | 3/2005 | Jahng |
| 2005/0065516 A1 | 3/2005 | Jahng |
| 2006/0052785 A1 * | 3/2006 | Augostino et al. ............ 606/61 |
| 2006/0058791 A1 * | 3/2006 | Broman et al. ................. 606/61 |
| 2007/0088359 A1 * | 4/2007 | Woods et al. .................. 606/61 |

OTHER PUBLICATIONS

Pass® Deformity System, Encore Surgical, © Jan. 2002.

Spine Internal Fixation Device, Encore Surgical, © Jan. 2002.

* cited by examiner

US 7,695,499 B2

SYSTEM, DEVICES AND METHOD FOR AUGMENTING EXISTING FUSION CONSTRUCTS

BACKGROUND

The present invention relates to prosthetic device implantation, and more particularly, but not exclusively, relates to techniques to augment a prior spinal fusion and implant construct.

The use of prosthetic implants to address orthopedic injuries and ailments has become commonplace. Nonetheless, there is an ever-present challenge to enable less invasive surgical techniques, shorten the time required to surgically implant prosthetic devices, decrease surgery recovery time, and/or provide other improvements. On occasion, there is also a need to augment prior spinal surgical procedures and/or implants. Thus, additional contributions in this area of technology remain welcome.

SUMMARY

One embodiment of the present application is a unique spinal implantation technique. Other embodiments include unique methods, systems, devices, kits, tools, instrumentation, and apparatus involving implantation of a prosthetic device to augment prior spinal surgery.

A further embodiment includes: evaluating a patient having a previously implanted spinal construct and corresponding spinal fusion from an earlier procedure, determining a spinal segment adjacent to the spinal fusion is degenerating after completion of the earlier procedure, and replacing a member of the previously implanted spinal construct with a flexible polymer elongated member by engaging the flexible polymer elongated member to one or more fasteners of the previously implanted spinal construct and attaching the flexible polymer elongated member to the spinal segment adjacent to the spinal fusion. In one form, this elongated member is at least partially comprised of polyetheretherketone (PEEK).

Another embodiment of the present application includes: evaluating a patient having a previously implanted spinal construct and corresponding spinal fusion from an earlier procedure; determining a spinal segment adjacent to the spinal fusion is degenerating after completion of the earlier procedure, coupling a crosslink to members of the previously implanted spinal construct, and attaching a flexible polymer elongated member to the crosslink and to the spinal segment adjacent to the spinal fusion with a first bone screw.

Still another embodiment includes: evaluating a patient having a previously implanted spinal construct and corresponding spinal fusion from an earlier procedure, determining a spinal segment adjacent to the spinal fusion is degenerating after completion of the earlier procedure, and augmenting the previously implanted spinal construct by attaching a flexible polymer elongated member to the spinal segment adjacent to the spinal fusion and by coupling the flexible polymer elongated member to one or more elements of the previously implanted spinal construct.

Yet another embodiment is a construct that includes a crosslink connected across two members and one or more flexible polymer elongated members connected to the crosslink between the members. The one or more flexible polymer elongated members are arranged to provide legs that diverge away from one another as each extends away from the crosslink. These legs each are further connected to a corresponding bone fastener that is structured to engage bone. In one form, the legs each have one or more bends between the crosslink and the corresponding bone fastener, and each corresponding bone fastener includes a pedicle screw.

A still further embodiment is an elongated member at least partially comprised of PEEK that carries a plurality of metallic sleeves. In one form, these sleeves each slide along the elongated member over at least a portion of its length. Alternatively or additionally, the sleeves are each attached to a respective connector that engages a patient's spine.

One object of the present application is to provide a unique spinal implantation technique.

Alternatively or additionally, another object of the present application is to provide a unique method, system, device, kit, tool, instrument, and/or apparatus involving spinal surgery augmentation.

Further embodiments, forms, features, aspects, benefits, objects, and advantages of the present application shall become apparent from the detailed description and figures provided herewith.

DETAILED DESCRIPTION OF SELECTED EMBODIMENTS

Figure 1:
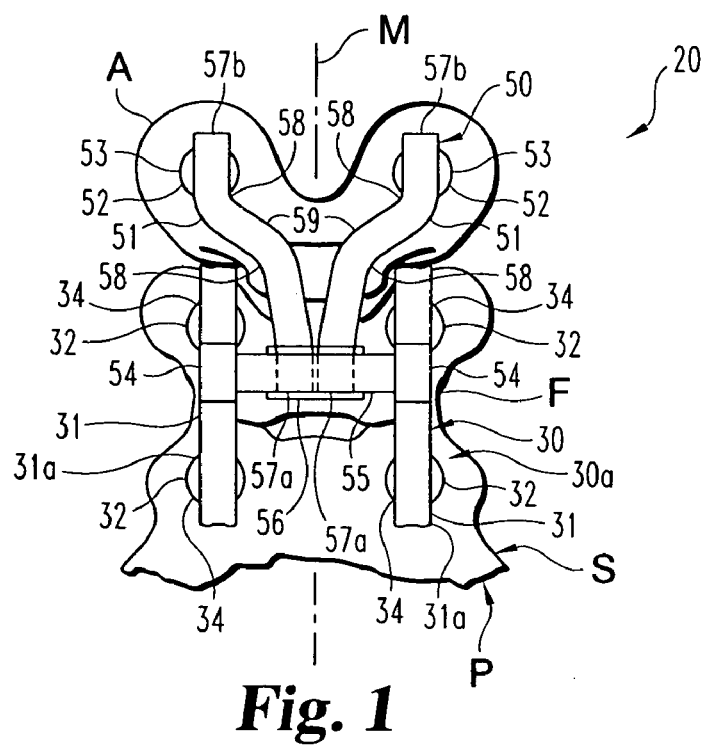
FIG. 1 is a partial posterior view of one type of spinal augmentation implant system relative to the spine of patient.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 illustrates spinal implant augmentation system 20 for spine S of patient P as viewed from the posterior along medial axis M. System 20 includes a previously implanted spinal construct 30 that resulted in spinal fusion F of spine S. Construct 30 includes several interconnected elements 30a, such as elongated members 31 in the form of rods 31a. Elements 30a of construct 30 also include two bone fasteners 32 fixed to each of rods 31a. Fasteners 32 each include bone screw 34 threaded into bone of spine S.

System 20 also includes augmentation construct 50. Construct 50 includes flexible polymer elongated members 51 that are each at least partially comprised of polyetheretherketone (PEEK) material, such as that provided by VICTREX, having an address of Victrex Technology Centre, Hillhouse International, Thornton Cleveleys, Lancashire FY5 4QD. Construct 50 includes bone fasteners 52 that each includes a pedicle bone screw 53. Pedicle bone screws 53 are each threaded into a pedicle of adjacent spinal segment A. Spinal segment A is next to fusion F. In one application, construct 50 is added to construct 30 to address degeneration of spinal segment A.

Construct 50 further includes connectors 54 and crosslink 55. Connectors 54 attach opposing ends of crosslink 55 to members 31 of construct 30. Crosslink 55 is also connected to elongated members 51 by connector 56 that is positioned between members 31 and connectors 54. Elongated members 51 each include end portion 57a opposite end portion 57b. Elongated members 51 diverge from one another relative to a pathway from end portion 57a towards end portion 57b, and are alternatively designated legs 59. Along this pathway, elongated members 51 each are shaped with two turns or bends 58; however, in other embodiments there may be more or fewer bends, if any. End portions 57b of elongated members 51 and fasteners 52 are each generally aligned with a corresponding rod 31a and its respective fasteners 32. Elongated members 51 are generally symmetric along a plane perpendicular to the view plane of FIG. 1 that is also coincident with medial axis M.

Figure 2:
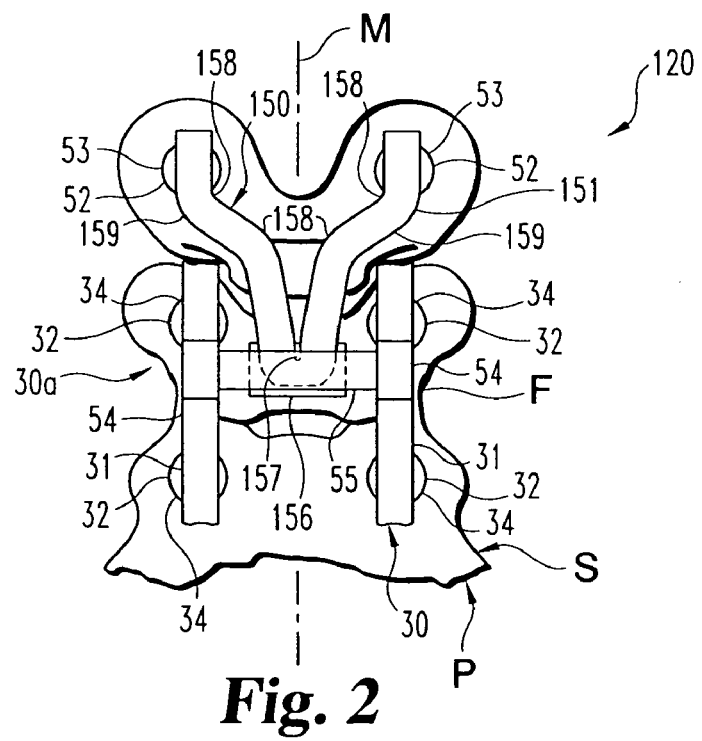
FIG. 2 is a partial posterior view of another type of spinal augmentation implant system relative to the spine of patient.

FIG. 2 illustrates another augmentation system 120 relative to spine S of patient P that extends along medial axis M; where like reference numerals refer to like features. System 120 includes previously implanted spinal construct 30 as described in connection with FIG. 1. In place of augmentation construct 50, system 120 includes augmentation construct 150. Like augmentation construct 50, construct 150 includes crosslink 55 connected at opposite ends to members 31 by connectors 54. Unlike construct 50, construct 150 includes flexible polymer elongated member 151 with a central bend 157 in addition to bends 158. At central bend 157, elongated member 151 is coupled to crosslink 55 by connector 156. Elongated member 151 is shaped with legs 159 that diverge from one another as they extend away from crosslink 55. Elongated member 151 is also symmetric about a plane through medial axis M that is approximately perpendicular to the view plane of FIG. 2 and generally aligns with members 31 and corresponding fasteners 32 where connected to spinal segment A by fasteners 52. Elongated member 151 also is at least partially comprised of PEEK material.

For construct 150, fasteners 52 again include pedicle bone screws 53 engaging pedicles of spinal segment A. Connections to fastener 52 and/or crosslink 55 can be provided in any form, including, but not limited a rigid, hinged, multiaxial, and/or spherical configuration, to name a few representative examples. Alternatively or additionally, connections can include a tether, a fluid filled dashpot, or the like.

Figure 3:
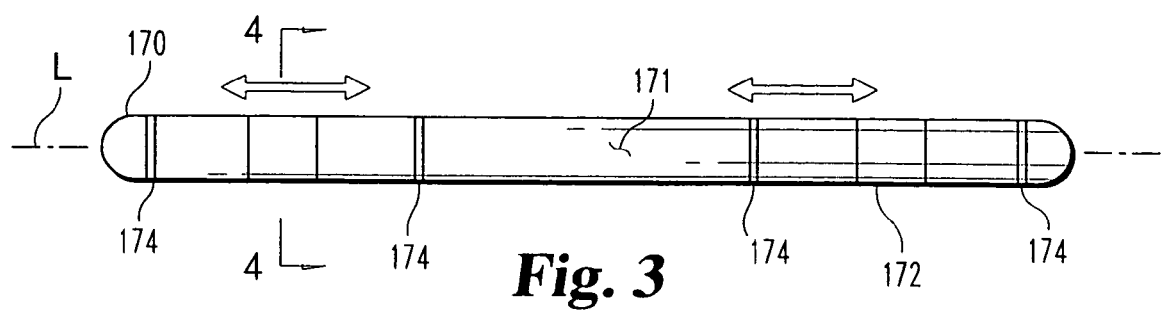
FIG. 3 is a diagrammatic view of a flexible elongated member for spinal constructs.
Figure 4:
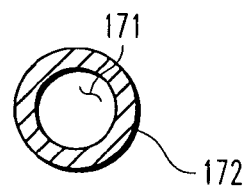
FIG. 4 is sectional view of the elongated member of FIG. 3 corresponding to section line 4-4 shown in FIG. 3.

FIGS. 3 and 4 illustrate flexible and elastic elongated member 170 for spinal implantation that has longitudinal axis L. Elongated member 170 is at least partially comprised of PEEK material 171. Elongated member further includes metallic sleeves 172 that are sized to slide along the elongated member 170 between slide stops 174 with a relatively snug fit, as represented by double-headed arrows in FIG. 3. In one application, sleeves 172 are engaged by a construct fastener (not shown) that constricts sleeve 172 in such a manner that is generally fixes the sleeve position along elongated member 170. FIG. 4 provides a sectional view of elongated member 170 corresponding to section line 4-4 shown in FIG. 3, which illustrates that sleeves 172 are generally concentric, and that elongated member 170 has an approximately circular cross section. In other forms, sleeves 172 may be differently composed and/or may be nonslidable—that is fixed in position along elongated member 172.

In one form, elongated members 51, 151, and 170 each essentially consist of PEEK with the optional exception of connection sites and sleeves such as sleeves 172. Indeed, particular alternative embodiments elongated member 51 and/or elongated member 151 each include metallic sleeves. In other embodiments, as an alternative or addition to PEEK, elongated members 51, 151, and/or 170 are made of a different material that is flexible and relatively elastic compared to elongated members of a previously implanted construct. Such different material includes one or more of a metallic alloy, a polyetherketoneketoneetherkeytone (PEKKEK), an ultra-high molecular weight polyethylene (UHMWPE), or a different thermoplastic or thermoset polymeric resin as would occur to those skilled in the art. Alternatively or additionally, elongated members 51, 151, and/or 170 can be structurally arranged to provide a desired elasticity and/or flexibility, such as a braid or laminate of different materials, an elongated member having an inner core and outer layer(s) composed of different materials, a shape memory configuration, or the like. In one form, elongated members 51, 151, and/or 170 are a type of rod having a generally cylindrical shape with a circular cross section; however, different shapes and corresponding cross sections can be used in different embodiments, forms, or variations. Furthermore, flexible polymer elongated members with changing shapes and/or cross sections can be employed in other embodiments.

Figure 5:
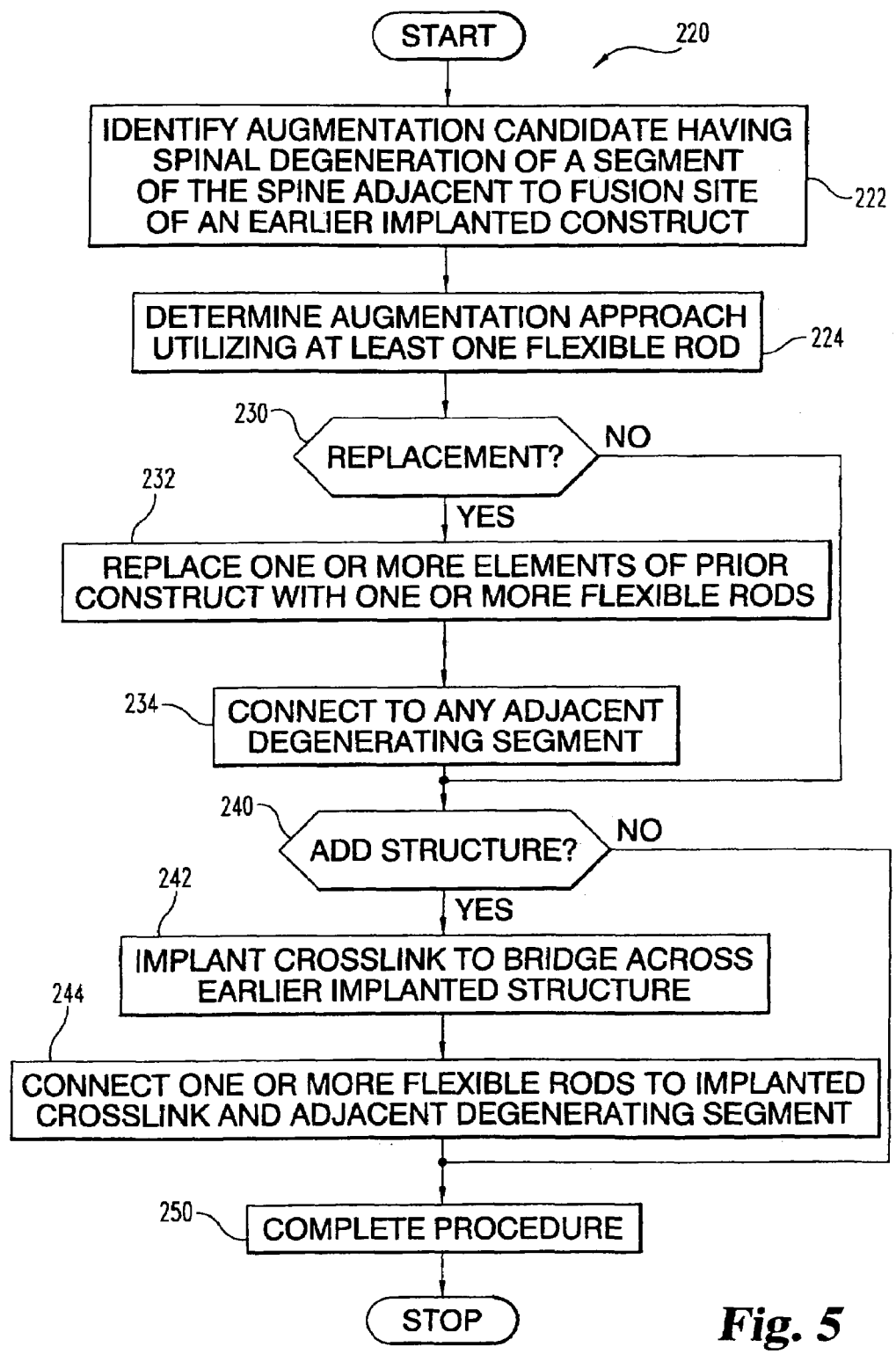
FIG. 5 is a flow chart of a spinal augmentation procedure.
Figure 6:
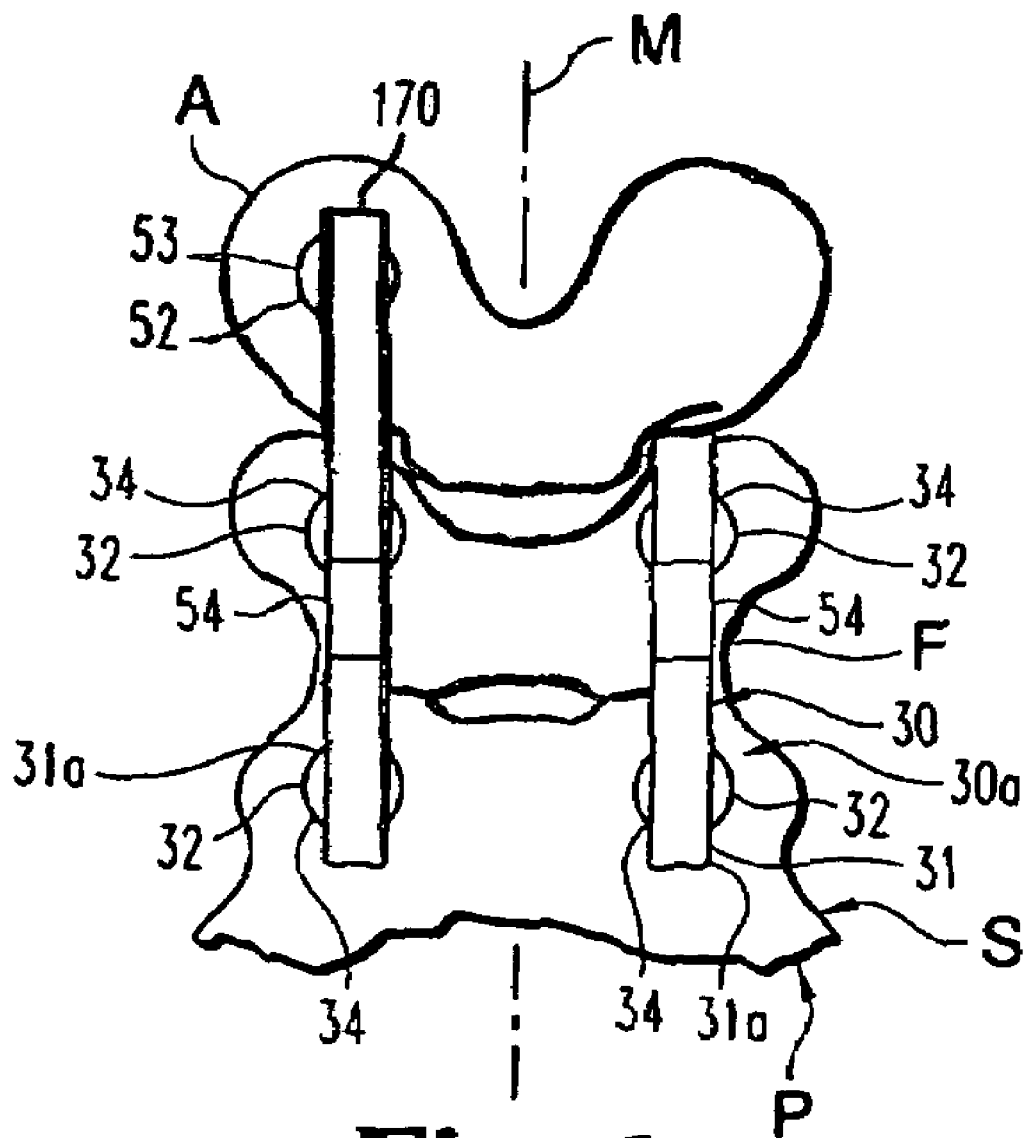
FIG. 6 is a partial posterior view of another type of spinal augmentation implant system.

FIG. 5 is a flowchart directed to spinal augmentation procedure 220. In stage 222 of procedure 220, a patient is identified that is experiencing degeneration of a spinal segment adjacent to a spinal fusion from a previously implanted spinal construct, such as construct 30. In stage 224, a physician determines and plans the implantation of an augmentation procedure that utilizes at least one flexible polymer rod or other type of elongated member. As part of the evaluation in stage 224, the physician decides whether to replace a previously implanted construct element, as represented by decision stage 230. As shown in FIG. 6, if a replacement is indicated (the "yes" branch from stage 230), procedure 220 continues in stage 232 with the substitution of at least one element, such as rod 31a of construct 30 (see FIG. 1), with a flexible polymer elongated member, such as elongated member 170, which is more specifically designated in the form of a rod in the FIG. 5 description of stage 232 but should not be limited to such form. In stage 234, the replacement elongated member is connected to the adjacent degenerating spinal segment. The replacement of a more rigid elongated member of a previously implanted construct with a more flexible elongated member is arranged to provide further loading on the existing fusion mass in such a manner that more mature bone is created in response.

If replacement is not indicated as tested by stage 230 (the "no" branch from stage 230), procedure 220 bypasses stages 232 and 234 and proceeds directly to decision stage 240. Stage 240 is also reached after stage 234 is executed. Stage 240 tests whether to add a further construct, such as construct 50 or 150, to the previously implanted construct, such as construct 30. If addition is indicated (the "yes" branch from stage 240), procedure 220 continues with stage 242. In stage 242, a crosslink is implanted to bridge across members of the earlier implanted structure. One or more flexible polymer elongated members are connected to the crosslink and the adjacent degenerating spine segment in stage 244. In the FIG. 5 description of stage 244, these elongated members are more specifically designated as rods, but should not be limited to such form. Stages 242 and 244 correspond to the addition of construct 50 or 150 of FIGS. 1 and 2; however, it should be appreciated that many other augmenting structures can be added as an alternative to either of these in other embodiments of procedure 220.

From stage 242, stage 250 is reached in which procedure 220 is completed. Stage 250 can also be reached directly from stage 240 if the test of stage 240 is negative (the "no" branch is followed), which bypasses stages 242 and 244. It should be appreciated that both replacement and addition can occur during procedure 220. Also, other constructs besides those illustrated herein can be used that include one or more flexible polymer elongated members.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A method, comprising:
    evaluating a patient having a previously implanted spinal construct and corresponding spinal fusion from an earlier procedure;
    determining a spinal segment adjacent to the spinal fusion is degenerating after completion of the earlier procedure; and
    after said determining, replacing at least one previously implanted member of the spinal construct with a flexible polymer elongated member by engaging the flexible polymer elongated member to one or more fastening devices of the previously implanted spinal construct and attaching the flexible polymer elongated member to the spinal segment adjacent to the spinal fusion with a bone fastener.

2. The method of claim 1, wherein the elongated member is at least partially comprised of PEEK.

3. The method of claim 1, wherein the bone fastener includes a bone screw.

4. The method of claim 1, wherein the elongated member is in a rod form and includes a number of sleeves, the one or more fastening devices each engaging a corresponding one of the sleeves.

5. The method of claim 4, wherein the sleeves are slidable along the elongated member before said engaging.

6. The method of claim 1, which includes implanting another flexible polymer elongated member in place of another member of the previously implanted spinal construct.

7. The method of claim 1, wherein the flexible polymer elongated member is formed of a material different from the material of the previously implanted member of the spinal construct.

8. The method of claim 7, wherein the material of the flexible polymer elongated member is relatively more flexible than the material of the previously implanted member of the spinal construct.

9. The method of claim 7, wherein the material of the flexible polymer elongated member is relatively more elastic than the material of the previously implanted member of the spinal construct.

10. The method of claim 1, wherein the flexible polymer elongated member is relatively more flexible than the previously implanted member of the spinal construct.

11. The method of claim 1, wherein the flexible polymer elongated member is relatively more elastic than the previously implanted member of the spinal construct.

12. A method, comprising:
    evaluating a patient having a previously implanted spinal construct and corresponding spinal fusion from an earlier procedure;
    determining a spinal segment adjacent to the spinal fusion is degenerating after completion of the earlier procedure; and
    after said determining, replacing at least one previously implanted member of the spinal construct with a flexible polymer elongated member by engaging the flexible polymer elongated member to one or more fastening devices of the previously implanted spinal construct and attaching the flexible polymer elongated member to the degenerating spinal segment adjacent to the spinal fusion with a newly implanted bone fastener, wherein the attaching comprises anchoring the newly implanted bone fastener to a pedicle of the degenerating spinal segment and engaging the elongated member to the newly implanted bone fastener.

13. The method of claim 12, wherein the bone fastener comprises a bone screw and wherein the anchoring comprises threading the bone screw into the pedicle.

14. The method of claim 13, wherein the one or more fastening devices of the previously implanted spinal construct comprise one or more bone screws and the engaging includes attaching the elongated member to the one or more bone screws.

15. A method, comprising:
    evaluating a patient having a previously implanted spinal construct and corresponding spinal fusion from an earlier procedure;
    identifying a degenerating spinal segment adjacent to the spinal fusion after completion of the earlier procedure; and
    after the identifying, replacing at least one previously implanted member of the spinal construct with a flexible polymer elongated member by, the replacing comprising:
        engaging the flexible polymer elongated member to one or more fastening devices of the previously implanted spinal construct;
        anchoring a newly implanted bone fastener to the degenerating spinal segment adjacent to the spinal fusion; and
        attaching the flexible polymer elongated member to the newly implanted bone fastener anchored to the degenerating spinal segment.

16. The method of claim 15, wherein the elongated member is at least partially comprised of PEEK.

17. The method of claim 15, wherein the elongated member is in a rod form and includes a number of sleeves, the one or more fastening devices each engaging a corresponding one of the sleeves.

18. The method of claim 15, which includes implanting another flexible polymer elongated member in place of another member of the previously implanted spinal construct.

19. The method of claim 15, wherein the newly implanted bone fastener comprises a bone screw and wherein the anchoring comprises threading the bone screw into the degenerating spinal segment.

20. The method of claim 15, wherein the flexible polymer elongated member is relatively more flexible than the previously implanted member of the spinal construct.

21. The method of claim 15, wherein the flexible polymer elongated member is relatively more elastic than the previously implanted member of the spinal construct.

* * * * *